US00PP14287P29

(12) United States Plant Patent
Parthasarathy et al.

(10) Patent No.: US PP14,287 P2
(45) Date of Patent: Nov. 11, 2003

(54) AGLAONEMA PLANT NAMED 'SILVERADO'

(50) Latin Name: *Aglaonema hybrida*
Varietal Denomination: Silverado

(76) Inventors: Gopalaswamy Parthasarathy, "Srinivasa", 237/46, Fifth Main Road, Chamrajpet, Bangalore 560018 (IN); Parthasarathy Mukundan, "Srinivasa", 237/46, Fifth Main Road, Chamrajpet, Bangalore 560018 (IN)

( * ) Notice: Subject to any disclaimer, the term of this patent is extended or adjusted under 35 U.S.C. 154(b) by 0 days.

(21) Appl. No.: 10/171,947

(22) Filed: Jun. 17, 2002

(51) Int. Cl.[7] ..... A01H 5/00
(52) U.S. Cl. ..... Plt./376
(58) Field of Search ..... Plt./376, 373

*Primary Examiner*—Bruce R. Campell
*Assistant Examiner*—June Hwu
(74) *Attorney, Agent, or Firm*—C. A. Whealy

(57) ABSTRACT

A distinct cultivar of Aglaonema plant named 'Silverado', characterized by its upright and outwardly arching growth habit; freely clumping habit; full and dense plant habit; long lanceolate leaves with acuminate apices; tri-colored leaves with a broad gray green central area with feathered edges surrounded by a darker gray green area that is surrounded by a distinct dark green margin; light green-colored leaf petioles; and low temperature tolerance.

1 Drawing Sheet

Botanical classification/cultivar denomination: Aglaonema hybrida cultivar Silverado.

BACKGROUND OF THE INVENTION

The present Invention relates to a new and distinct cultivar of Aglaonema plant, botanically known as *Aglaonema hybrida* and hereinafter referred to by the name 'Silverado'.

The new Aglaonema is the result of a planned breeding program conducted by the Inventors in Chamrajpet, Bangalore, India. The objective of the breeding program is to create new Aglaonema cultivars with compact and dense plant habit, unique leaf variegation patterns, interesting leaf shapes, resistance to pathogens, and tolerance to low temperatures.

The new Aglaonema originated from a cross made by the Inventors on or about Aug. 19, 1988 of the *Aglaonema nitidum f. cinereum* cultivar Ernesto's Favorite, not patented, as the female, or seed, parent with a proprietary selection of *Aglaonema hybrida* identified as code number KSG Hybrid 86-31, not patented, as the male, or pollen, parent. The new Aglaonema was discovered and selected by the Inventors in 1989 as a single plant within the progeny of the stated cross in a controlled environment in Chamrajpet, Bangalore, India. The new Aglaonema was selected on the basis of its plant habit, leaf shape and unique tri-colored variegation pattern.

Asexual propagation of the new cultivar by cuttings or by divisions since March, 1990 in a controlled environment in Chamrajpet, Bangalore, India, has shown that the unique features of this new Aglaonema are stable and reproduced true to type in successive generations.

SUMMARY OF THE INVENTION

The following traits have been repeatedly observed and are determined to be the unique characteristics of 'Silverado'. These characteristics in combination distinguish 'Silverado' as a new and distinct cultivar:

1. Upright and outwardly arching growth habit.
2. Freely clumping habit, full and dense plants.

3. Long lanceolate leaves with acuminate apices.
4. Tri-colored leaves with a broad gray green central area with feathered edges surrounded by a darker gray green area that is surrounded by a distinct dark green margin.
5. Light green-colored leaf petioles.
6. Low temperature tolerance.

In side-by-side comparisons conducted by the Inventors in Chamrajpet, Bangalore, India, plants of the new Aglaonema differed from plants of the female parent, the *Aglaonema hybrida* cultivar Ernesto's Favorite, in the following characteristics:

1. Plants of the new Aglaonema were freely-clumping and produced many more offshoots per plant than plants of the cultivar Ernesto's Favorite.
2. Plants of the new Aglaonema had more leaves and were more dense than plants of the cultivar Ernesto's Favorite.
3. Leaves of plants of the new Aglaonema and the cultivar Ernesto's Favorite differed in leaf variegation pattern and color as leaves of plants of the cultivar Ernesto's Favorite were bi-colored with gray green centers surrounded by dark green extending to the margins.

In side-by-side comparisons conducted by the Inventors in Chamrajpet, Bangalore, India, plants of the new Aglaonema differed from plants of the male parent, the *Aglaonema hybrida* selection KSG hybrid 86-31, in the following characteristics:

1. Plants of the new Aglaonema were freely-clumping and produced more offshoots per plant than plants of the selection KSG hybrid 86-31.
2. Plants of the new Aglaonema had more leaves and were more dense than plants of the selection KSG hybrid 86-31.
3. Plants of the new Aglaonema grew faster than plants of the selection KSG hybrid 86-31.
4. Leaves of plants of the new Aglaonema were long and lanceolate in shape whereas leaves of plants of the selection KSG hybrid 86-31 were broad and obovate in shape.

5. Leaves of plants of the new Aglaonema and the selection KSG hybrid 86-31 differed in leaf variegation pattern and color as leaves of plants of the selection KSG hybrid 86.31 had chartreuse green leaves overlain with irregular gray green patches and pale yellow random spots.

Plants of the new Aglaonema can be compared to plants of the cultivar 39303, disclosed in U.S. Plant Pat. No. 10,140. In side-by-side comparisons conducted in Homestead, Fla., plants of the new Aglaonema differed from plants of the Aglaonema cultivar 39303 in the following characteristics:

1. Plants of the new Aglaonema were more compact than plants of the cultivar 39303.
2. Leaves of plants of the new Aglaonema were more narrow and had shorter petioles than leaves of plants of the cultivar 39303.
3. Leaves of plants of the new Aglaonema and the cultivar 39303 differed in leaf variegation pattern and color as plants of the cultivar 39303 had gray and green leaves with random gold speckling.
4. Leaves of plants of the new Aglaonema had light green-colored petioles whereas plants of the cultivar 39303 had white-colored petioles.

Plants of the new Aglaonema can also be compared to plants of the cultivar Silver Bay, not patented. In side-by-side comparisons conducted in Homestead, Fla., plants of the new Aglaonema differed from plants of the Aglaonema cultivar Silver Bay in the following characteristics:

1 Plants of the new Aglaonema were more compact than plants of the cultivar Silver Bay.
2. Leaves of plants of the new Aglaonema were more narrow and had shorter petioles than leaves of plants of the cultivar Silver Bay.
3. Leaves of plants of the new Aglaonema and the cultivar Silver Bay differed in leaf variegation pattern and color as plants of the cultivar Silver Bay had gray and dark green bi-colored leaves.
4. Leaves of plants of the new Aglaonema had light green-colored petioles whereas plants of the cultivar Silver Bay had green and white bi-colored petioles.

BRIEF DESCRIPTION OF THE PHOTOGRAPHS

The accompanying colored photographs illustrate the overall appearance of the new Aglaonema, showing the colors as true as it is reasonably possible to obtain in colored reproductions of this type. Colors in the photographs may differ slightly from the color values cited in the detailed botanical description which accurately describe the colors of the new Aglaonema.

The photograph at the top of the sheet comprises a side perspective view of a typical plant of 'Silverado'.

The photograph at the bottom of the sheet comprises a close-up view of the upper surface of a typical leaf of the new Aglaonema.

DETAILED BOTANICAL DESCRIPTION

The cultivar Silverado has not been observed under all possible environmental conditions. The phenotype may vary somewhat with variations in environment such as temperature and light intensity without, however, any variance in genotype.

The aforementioned photographs and following observations and measurements describe plants of the new Aglaonema that were grown in 25-cm containers, in Homestead, Fla., in a polypropylene-covered shadehouse with light levels about 2,500 foot-candles. During the production of the plants, day temperatures ranged from 5 to 40° C. and night temperatures ranged from 5 to 30° C. Plants used for the photographs and description were about 19 months from planting. Color references are made to The Royal Horticultural Society Colour Chart except where general terms of ordinary dictionary significance are used.

Botanical classification: *Aglaonema hybrida* cultivar Silverado.

Parentage:

*Female, or seed, parent.*—*Aglaonema nitidum f. cinereum* cultivar Ernesto's Favorite, not patented.

*Male, or pollen, parent.*—Proprietary selection of *Aglaonema hybrida* identified as code number KSG hybrid 86-31, not patented.

Propagation:

*Type.*—By cuttings.

*Time to initiate roots.*—Summer: About 18 to 20 days at 25 to 36° C. Winter: About 30 to 35 days at 15 to 28° C.

*Time to produce a rooted plant.*—Summer: About 30 to 35 days at 25 to 36° C. Winter: About 40 to 45 days at 15 to 28° C.

*Root description*—Thick, fibrous, fleshy, and freely-branching.

Plant description:

*Appearance.*—Erect when young, becoming outwardly arching as leaves develop; inverted triangle, symmetrical. Freely clumping habit give plants a very fully and dense appearance. Appropriate for 25-cm containers.

*Plant height.*—About 52 cm.

*Plant width.*—About 74 cm.

*Growth rate/vigor.*—Vigorous, relatively rapid growth rate.

*Stem color.*—Close to 144A.

*Branching habit.*—Freely clumping habit; plants typically produce about 15 offshoots per plant; full and dense plants.

*Foliage description.*—Length: About 32.3 cm. Width: About 12.4 cm. Shape: Lanceolate. Apex: Acuminate. Base: Obtuse. Margin: Entire, slightly undulating. Orientation: Initially upright to outwardly arching. Aspect: Concave. Texture: Mostly smooth, slightly rugose; glabrous; thick and leathery. Veins: Slightly recessed on upper surface and prominent on lower surface. Color: Young leaves, upper surface: Center, light green, closest to 148C; surrounded by darker green, close to 144A; margin, between 144A and 146A; shiny. Young leaves, lower surface: Close to 146B to 146C, shiny. Fully expanded leaves, upper surface: Center, gray green, closest to 191A, surrounded by darker gray green, between 191A and 189A; margin, dark green, 147A; shiny. Fully expanded leaves, lower surface: Closest to 146A to 147B, shiny. Venation, upper surface: Same as ground color. Venation, lower surface: Close to 146B. Petiole: Length: About 17 cm. Diameter, at leaf base: About 25 cm. Diameter, base: About 1.8 cm. Wing length: About 11 cm. Wing width, at base: About 1.1 cm. Color: Mostly 146A to 146B; towards the base of the plant, 146C to 146D.

Inflorescence description: Inflorescence development has not been observed on plants of the new Aglaonema grown under shadehouse production conditions.

Disease/pest resistance: Plants of the new Aglaonema have been observed to be resistant to pathogens common to Aglaonema such as Xanthomonas and Fusarium. Plants of the new Aglaonema have not been observed to be resistant to pests common to Aglaonema.

Weather tolerance: Plants of the new Aglaonema have been observed to be tolerant to wind, rain and temperatures ranging from 5 to 40° C.

It is claimed:

1. A new and distinct cultivar of Aglaonema plant named 'Silverado', as illustrated and described.

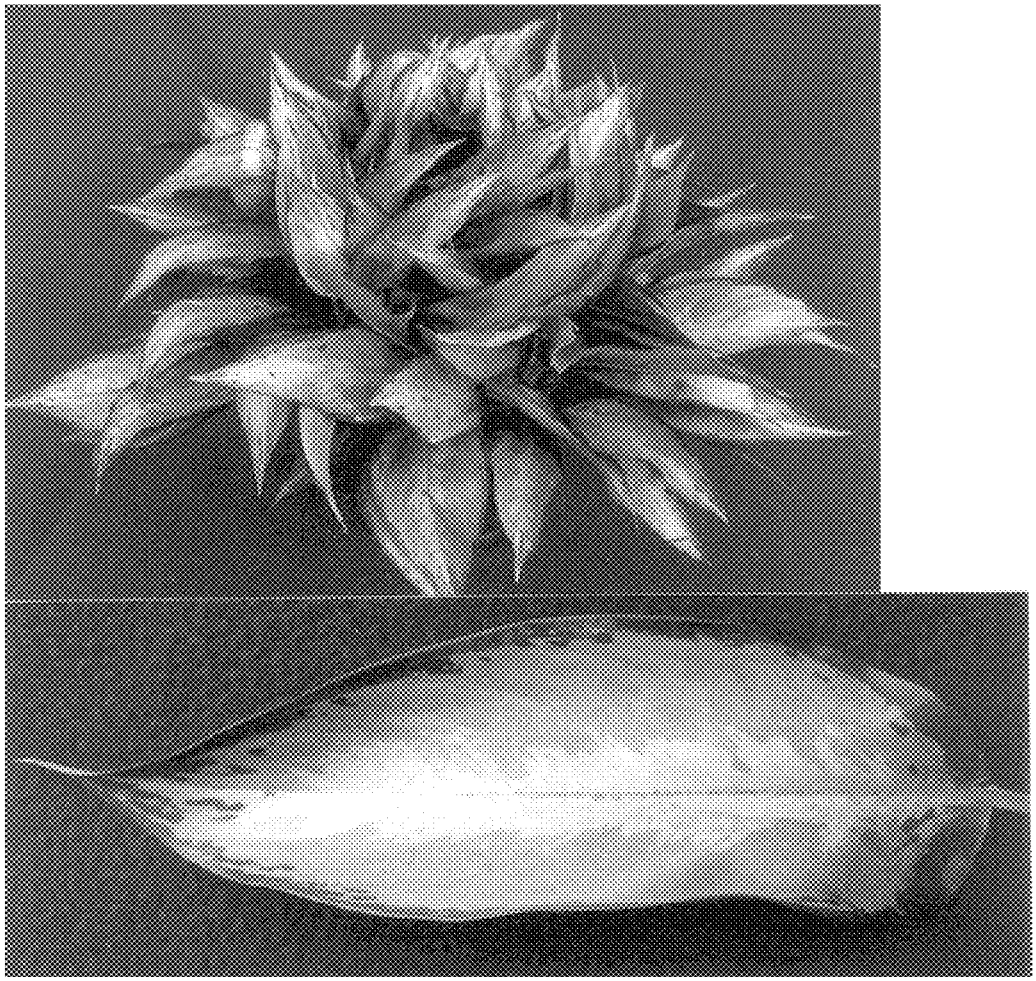

* * * * *